United States Patent [19]
Hamblin, Jr. et al.

[11] Patent Number: 6,033,419
[45] Date of Patent: Mar. 7, 2000

[54] APPARATUS AND METHOD FOR CUTTING A HEART VALVE ANNULUS

[75] Inventors: James Henry Hamblin, Jr., Lockhart; Billy Ray Singleton, Georgetown, both of Tex.

[73] Assignee: Sulzer Carbomedics Inc., Austin, Tex.

[21] Appl. No.: 09/079,796

[22] Filed: May 15, 1998

[51] Int. Cl.⁷ .................................................. A61B 17/34
[52] U.S. Cl. .......................................... 606/184; 606/185
[58] Field of Search .................................. 606/184, 185, 606/180, 167, 170, 187

[56] References Cited

U.S. PATENT DOCUMENTS

| | | | |
|---|---|---|---|
| 3,776,237 | 12/1973 | Hill et al. ................................. | 128/305 |
| 4,018,228 | 4/1977 | Goosen .................................... | 606/184 |
| 5,069,679 | 12/1991 | Taheri ..................................... | 606/159 |
| 5,129,913 | 7/1992 | Ruppert .................................... | 606/184 |
| 5,690,662 | 11/1997 | Chiu et al. ............................... | 606/184 |
| 5,827,316 | 10/1998 | Young et al. ............................. | 606/184 |

FOREIGN PATENT DOCUMENTS

| | | |
|---|---|---|
| 2028070 | 12/1971 | Germany . |
| 19507560 | 9/1996 | Germany . |
| WO 9516476 | 6/1995 | WIPO . |
| WO 9727799 | 8/1997 | WIPO . |

*Primary Examiner*—Michael Buiz
*Assistant Examiner*—Kevin Truong
*Attorney, Agent, or Firm*—Timothy L. Scott; Philip S. Lyren

[57] ABSTRACT

An apparatus and method are disclosed for cutting a heart valve annulus. The apparatus includes an actuator and a backup plate coupled to the actuator. The apparatus also includes an annulus cutter movably coupled to the actuator. The annulus cutter can thereby oppose and engage the backup plate. The method includes positioning a backup plate proximate heart valve tissue to be removed. An annulus cutter is then positioned proximate the heart valve tissue opposing the backup plate. The annulus cutter is engaged in opposition with the backup plate to cut the heart valve tissue and form a heart valve annulus. The heart valve tissue is then removed.

19 Claims, 1 Drawing Sheet

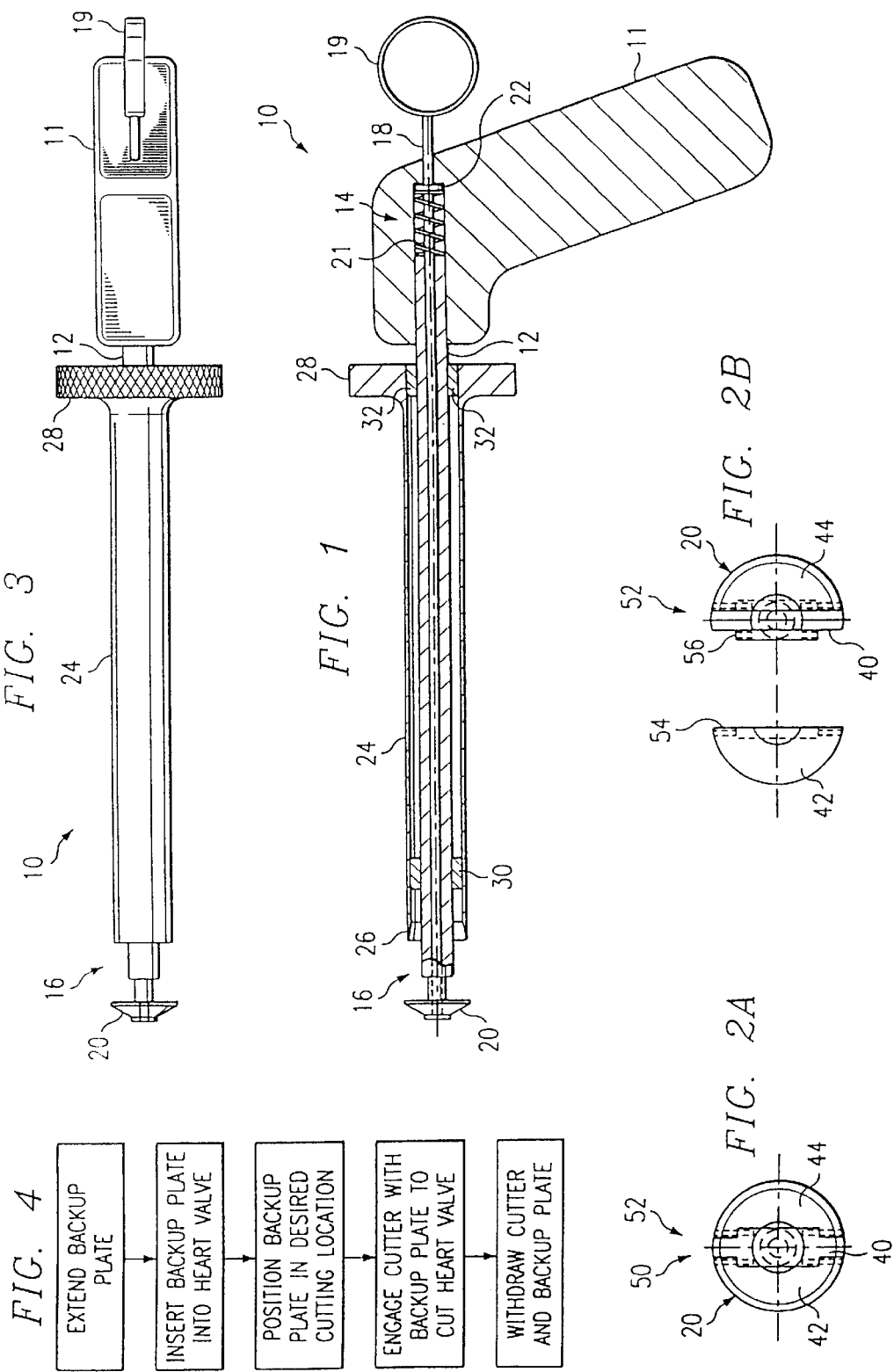

APPARATUS AND METHOD FOR CUTTING A HEART VALVE ANNULUS

TECHNICAL FIELD OF THE INVENTION

This invention relates in general to the field of medical devices and, more particularly, to an apparatus and method for cutting a heart valve annulus.

BACKGROUND OF THE INVENTION

The surgical procedure for heart valve replacement typically involves removal of a diseased heart valve and implantation of an artificial heart valve device. Removal of the diseased heart valve generally involves cutting the valve from the heart to form an annulus in which the replacement valve is implanted. Conventional cutting processes for forming the heart valve annulus involve the use of scissor devices to cut the existing valve tissue from the heart.

This conventional use of scissors often produces imprecise cuts and leaves an irregular annulus in which the surgeon must then attach the replacement valve. Typically, attachment of the replacement valve is accomplished by suturing a sewing cuff to the valve annulus. Because of the irregular annulus left by the use of scissors, the suturing process can be quite time consuming. In particular, the surgeon must insure that there are no openings around the replacement valve that would allow blood to flow from the heart chamber without passing through the replacement valve.

SUMMARY OF THE INVENTION

In accordance with the present invention, an apparatus and method are disclosed for cutting a heart valve annulus that provide advantages over conventional heart valve removal devices and procedures.

According to one aspect of the present invention, an apparatus for cutting a heart valve annulus includes an actuator and a backup plate coupled to the actuator. The apparatus also includes an annulus cutter movably coupled to the actuator. The annulus cutter can thereby oppose and engage the backup plate.

In one embodiment, the apparatus also includes a handle, a body and a spring. The body has a first end coupled to the handle, and the actuator extends through the body. The spring has a compressed state allowing the backup plate to be extended from the body and has an uncompressed state holding the backup plate in contact with the body.

In another embodiment, the apparatus further includes a cutter member movably coupled to the body and positioned coaxially with respect to the body and the actuator. In this embodiment, the annulus cutter is coupled to a first end of the cutter member proximate the backup plate.

According to another aspect of the present invention, a method is provided for cutting a heart valve annulus. The method includes positioning a backup plate proximate heart valve tissue to be removed. An annulus cutter is then positioned proximate the heart valve tissue opposing the backup plate. The annulus cutter is engaged in opposition with the backup plate to cut the heart valve tissue and form a heart valve annulus. The heart valve tissue is then removed.

A technical advantage of the present invention is the ability to more quickly remove a diseased heart valve and to make a more uniform heart valve annulus for receiving a replacement valve. This leads to less time in the operating room, thus less trauma to the patient.

Another technical advantage is that the apparatus can be sized to match standard sizes for replacement heart valves such that the heart valve annulus is the correct size for the replacement valve. Further, the apparatus can be manufactured at a relatively low cost which makes it economical to make a disposable set matching all standard sizes for replacement valves.

Other technical advantages of the present invention should be readily apparent to one of skill in the art in view of the drawings, description and claims.

BRIEF DESCRIPTION OF THE DRAWINGS

A more complete understanding of the present invention and advantages thereof may be acquired by referring to the following description taken in conjunction with the accompanying drawings, in which like reference numbers indicate like features, and wherein:

FIG. 1 is a cross section view of one embodiment of an apparatus for cutting a heart valve annulus according to the present invention;

FIGS. 2A and 2B are a top view and an exploded view of the collapsible backup plate of the apparatus of FIG. 1;

FIG. 3 is top view of the apparatus of FIG. 1; and

FIG. 4 is a flow chart of one embodiment of a method for cutting a heart valve annulus according to the present invention.

DETAILED DESCRIPTION OF THE INVENTION

FIG. 1 is a cross section view of one embodiment of an apparatus, indicated generally at 10, for cutting a heart valve annulus according to the present invention. Apparatus 10 of FIG. 1 comprises a handle 11 and a body 12 coupled to handle 11. Body 12 has first end 14 fixedly coupled to handle 11 and a second end 16. Second end 16 can be tapered, as shown. In the illustrative embodiment, body 12 has a cylindrical shape and is hollow. An actuator 18 extends through handle 11 and through the inside of body 12. In the illustrative embodiment, actuator 18 is a cylindrical rod having a ring 19 attached to one end. The other end of actuator 18 is coupled to a collapsible backup plate 20.

Collapsible backup plate 20 can be moved with respect to body 12 by movement of actuator 18. As shown, a spring 21 is positioned inside body 12 at first end 14. Spring 21 engages body 12 and has a plate 22 that is coupled to actuator 18. When actuator 18 is used to move backup plate 20 away from body 12, spring 21 is compressed. When actuator 18 is released, spring 21 expands and moves backup plate 20 back in contact with end 16 of body 12. When extended, backup plate 20 is free to collapse, and when released, backup plate 20 is held open by end 16 of body 12.

Apparatus 10 has a cutter member 24 positioned coaxially around body 12. Cutter member 24 is cylindrical with a hollow interior. In the embodiment of FIG. 1, cutter member 24 has an annulus cutter 26 at one end and a cutter rotator 28 at the other end. Annulus cutter 26 can, for example, be a stainless steel cutting tip coupled to the end of cutter member 24. A pair of bushings 30 and 32 are positioned between cutter member 24 and body 12 and allow cutter member 24 to slide along body 12.

During a heart valve replacement procedure, a surgeon can use apparatus 10 to remove the existing heart valve and form a heart valve annulus for receiving the replacement valve. The surgeon can compress actuator 18 to extend backup plate 20. The surgeon can then insert backup plate 20 through the existing valve into the heart chamber. Once backup plate 20 is positioned behind the existing valve, the surgeon can release actuator 18 such that backup plate 20 is held in contact with end 16 of body 12 by the action of spring 21. The surgeon can then slide cutter member 24 using cutter rotator 28 until annulus cutter 26 engages the existing valve and opposes collapsible backup plate 20. Once annulus cutter 26 is positioned accurately, the surgeon can remove the existing valve by rotating cutter member 24 and cutting through the existing valve until annulus cutter 26 contacts backup plate 20. At this point, the existing heart valve has been removed and a heart valve annulus has been formed. The removed tissue is held by annulus cutter 26 and collapsible backup plate 20. The surgeon can then remove apparatus 10 from the patient and thereby also remove the existing heart valve.

The use of apparatus 10 allows the surgeon to quickly and cleanly remove the existing valve and form the valve annulus to receive a replacement heart valve. Further, annulus cutter 26 and backup plate 20 can be sized as appropriate for the particular replacement valve. In one implementation, an apparatus 10 is constructed for each potential valve size. The surgeon then selects the appropriate apparatus 10 according to the size of the valve the surgeon decided to implant. Further, apparatus 10 can be constructed primarily from injection molded plastic except for annulus cutter 28 which can be stainless steel. This allows apparatus 10 to be disposable. Also, it should be understood that numerous other implementations exist for actuating backup plate 20 and cutter member 24. Further, it is possible for the annulus cutter 26 and backup plate 20 to be switched such that the cutting edge is pressed down into the heart valve and then pulled back to engage the heart valve and backup plate for cutting.

FIG. 2A is a top view of collapsible backup plate 20 of FIG. 1. As shown, backup plate 20 includes a centerpiece 40 having a leaflet 42 and leaflet 44 coupled thereto. In this embodiment, leaflets 42 and 44 are coupled to centerpiece 40 by hinges 50 and 52. This allows leaflets 42 and 44 to hinge as backup plate 20 passes through the existing heart valve. The cross section can thereby be reduced such that backup plate 20 can more easily be inserted into the heart chamber and placed in position for cutting. However, it is possible to provide other mechanisms for collapsing backup plate 20 in addition to the hinged scheme of FIG. 2A. The illustrated embodiment is considered to be relatively inexpensive to manufacture and is thus chosen as apparatus 10 may be a disposable surgical device. Further, the apparatus can be built as a set of different sized cutter devices to facilitate different valve sizes. In such an implementation, each apparatus 10 would be replaceable thus avoiding any difficulties with sterilization due to bacteria traps within apparatus 10.

In operation, after the surgeon extends collapsible backup plate 20 away from body 12, leaflets 42 and 44 are free to move. As the surgeon passes backup plate 20 through the existing heart valve, leaflets 42 and 44 will hinge upward and reduce the cross section. Once in place, the surgeon can release actuator 18 such that backup plate 20 is pulled back into contact with body 12. This forces leaflets 42 and 44 back into the fully open position. As shown in FIG. 2A, actuator 18 can connect to centerpiece 40 inside of hinges 50 and 52. On the other hand, second end 16 of body 12 contacts leaflets 42 and 44 outside of hinges 50 and 52 such that body 12 causes leaflets to be held open when the two are engaged.

FIG. 2B is an exploded view of backup plate 20 of FIG. 1. As shown, hinge 50 can comprise two hinge sides 54 and 56. Hinge 50 can be formed using a pin to couple hinge side 54 with hinge side 56. This moveably couples leaflet 42 to centerpiece 40. Leaflet 44 can be similarly coupled to centerpiece 40.

FIG. 3 is a top view of apparatus 10 of FIG. 1. As shown, apparatus 10 includes body 12 having a first end 14 and second end 16. Actuator 18 extends through body 12 and connects at one end to a ring 19 and at the other end to backup plate 20. A cutter member 24 includes an annulus cutter 26 and a cutter rotator 28. Cutter member 24 is positioned coaxially with body 12 and is hollow.

In general, apparatus 10 provides an annulus cutter 26 in a hand held device which can engage a backup plate 20 for cutting a diseased heart valve. Backup plate 20 can be collapsible to pass through the diseased valve and can be operated using actuator 18. After passing through the valve, backup plate 20 can be opened inside the heart chamber. Annulus cutter 26 can then be moved toward backup plate 20 to engage the tissue to be removed and to be opposed by backup plate 20. Rotation of annulus cutter 26 by the surgeon can quickly cut the heart valve tissue and provide a uniform annulus for a replacement heart valve. Further, the removed tissue is captured by annulus cutter 26 and backup plate 20 and can be easily removed from the body. The uniform annulus then provides for easier and more accurate suturing of the replacement valve.

Other embodiments of apparatus 10 can be built that generally allow a backup plate and an annulus cutter to engage and cut a heart valve for removal. For example, the apparatus can be built as a flexible device that can be extended through an opening into the patient's body in a less invasive procedure. The device could be extended through a catheter or other conduit for a non-invasive surgical procedure. In such an embodiment, the annulus cutter and backing plate could be coaxially extended through the conduit and could be actuated from a remote point outside of the patient's body.

FIG. 4 is a flow chart of one embodiment of a method for cutting a heart valve annulus according to the present invention. As shown, in step 60, a backup plate can be extended. As mentioned above, this can be done to allow the backing plate to be flexible for a reduced cross section. Then, in step 62, the backup plate is inserted through the heart valve into the heart chamber. In step 64, the backup plate is positioned in the desired cutting location for removal of existing heart valve tissue. The surgeon, in step 66, engages an annulus cutter in opposition with the backup plate to cut and remove the existing heart valve tissue. The surgeon then withdraws the annulus cutter and backup plate from the patient in step 68. By providing a uniform cutting edge and a backup plate to oppose the cutting action, this method allows the surgeon to more quickly remove diseased heart valve tissue and to make a more uniform heart valve annulus for receiving a replacement valve. This method also allows the surgeon to more quickly attach the replacement valve because of the uniformity of the annulus. Consequently, the patient spends less time in the operating room and experiences less trauma.

Although the present invention has been described in detail, it should be understood that various changes, substitutions and alterations can be made hereto without departing from the spirit and scope of the invention as defined by the appended claims.

What is claimed is:

1. An apparatus for cutting a heart valve annulus, comprising:

an actuator having a first end and a second end;

an annulus cutter movably coupled to the actuator between the first end and the second end; and a backup plate coupled to the first end of the actuator, said backup plate comprising a stop for opposing and engaging said said annulus cutter.

2. The apparatus of claim 1, further comprising:

a handle;

a body having a first end and a second end, the first end coupled to the handle, and the actuator extending through the body;

a spring coupled to the body and to the actuator, the spring having a compressed state allowing the backup plate to be extended from the body and having an uncompressed state holding the backup plate in contact with the body.

3. The apparatus of claim 2, further comprising:

a cutter member movably coupled to the body and positioned coaxially with respect to the body and the actuator;

the annulus cutter coupled to a first end of the cutter member proximate the backup plate.

4. The apparatus of claim 3, wherein the annulus cutter comprises a stainless steel cutter.

5. The apparatus of claim 3, wherein the annulus cutter comprises a cutter edge formed integrally with the cutter member.

6. The apparatus of claim 3, further comprising:

a cutter rotator coupled to a second end of the cutter member distal from the backup plate; and a ring coupled to the second end of the actuator.

7. The apparatus of claim 1, wherein the apparatus is flexible and can be operated through a conduit in a non-invasive procedure.

8. The apparatus of claim 7, wherein the conduit is a catheter.

9. A method for cutting a heart valve annulus, comprising:

positioning an annulus cutter proximate heart valve tissue to be removed;

positioning a backup plate comprising a stop for the annulus cutter proximate the heart valve tissue;

engaging the cutter in opposition with the backup plate to cut the heart valve tissue and form a heart valve annulus; and removing the heart valve tissue.

10. The method of claim 9, wherein positioning the backup plate comprises extending the backup plate through an existing heart valve into a heart chamber.

11. The method of claim 9, wherein the backup plate is collapsible to form a smaller cross section.

12. The method of claim 9, wherein positioning the annulus cutter comprises moving the annulus cutter to contact the heart valve tissue outside the heart chamber.

13. The method of claim 9, wherein the annulus cutter is circular and forms a circular heart valve annulus.

14. The method of claim 9, wherein the backup plate and the annulus cutter are components of a hand-held surgical device.

15. The method of claim 9, wherein the backup plate and the annulus cutter are components of a flexible surgical device that can operated through a conduit in a non-invasive procedure.

16. An apparatus for cutting a heart valve annulus, comprising:

an actuator having a first end and a second end;

an annulus cutter movably coupled to the actuator between the first end and the second end; and a collapsible backup plate coupled to the first end of the actuator.

17. The apparatus of claim 16, wherein said collapsible backup plate further comprises:

a centerpiece;

a first leaflet movably coupled to the centerpiece; and a second leaflet movably coupled to the centerpiece.

18. The apparatus of claim 17, wherein the first and second leaflets are coupled to the centerpiece by hinges.

19. The apparatus of claim 17, wherein the leaflets are held in place when the backup plate is in contact with the body.

* * * * *